US 6,716,440 B2

(12) United States Patent
Aronson et al.

(10) Patent No.: US 6,716,440 B2
(45) Date of Patent: Apr. 6, 2004

(54) WET-SKIN TREATMENT COMPOSITIONS

(75) Inventors: Michael Paul Aronson, West Nyack, NY (US); Liang Sheng Tsaur, Norwood, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/425,206

(22) Filed: Apr. 29, 2003

(65) Prior Publication Data

US 2003/0190296 A1 Oct. 9, 2003

Related U.S. Application Data

(62) Division of application No. 10/050,280, filed on Jan. 16, 2002, now Pat. No. 6,645,511.

(51) Int. Cl.⁷ .......................... A61K 9/107; A61K 7/40; A61K 7/48

(52) U.S. Cl. ................. 424/401; 514/938; 514/844; 514/847

(58) Field of Search ............... 424/400–1; 514/937–38, 514/944–45, 947, 844, 847

(56) References Cited

U.S. PATENT DOCUMENTS

| 5,041,281 A | 8/1991 | Strobridge |
| 5,578,299 A | 11/1996 | Starch |
| 5,661,189 A | 8/1997 | Grieveson et al. |
| 5,928,632 A | 7/1999 | Reusch |

FOREIGN PATENT DOCUMENTS

| WO | 96/25144 | 8/1996 |
| WO | 02/092043 A2 | 11/2002 |

*Primary Examiner*—Edward J. Webman
(74) *Attorney, Agent, or Firm*—Ronald A. Koatz

(57) ABSTRACT

The invention provides wet skin treatment compositions for use during bathing. The compositions are activated by water and retained efficiently on skin. The compositions impart desirable benefits to skin, are perceived to absorb quickly on wet skin, and leave the skin feeling clean, but non-greasy.

5 Claims, No Drawings

WET-SKIN TREATMENT COMPOSITIONS

This is a Divisional application of Ser. No. 10/050,280, filed Jan. 16, 2002, now U.S. Pat. No. 6,645,511.

FIELD OF THE INVENTION

The present invention relates to wet-skin treatment compositions that are designed for use during bathing to impart desirable properties to the skin, help maintain its health and protect it from environmental stress. By using aqueous dispersions of specific structured oil phases, which satisfy specific criteria in tests defined herein, applicants have obtained compositions that are activated by water and retained efficiently on skin. More particularly, at least a portion of the structured oil phase comprises a dispersed phase which may in turn comprise inorganic particles, organic particles or droplets of water soluble ingredients.

These wet skin treatment compositions impart the noted desirable benefits to the skin and are perceived to absorb quickly on wet skin, thereby leaving the skin feeling clean and non-greasy after rinsing. Thus, the consumer obtains the benefit of oily benefit agent from the wash, but does not perceive "greasy" feeling often associated with the benefit agent even after rinsing.

BACKGROUND OF INVENTION

Compositions that can effectively moisturize and protect the skin during the bathing process while the skin is still wet are a potentially convenient, and time saving approach to skin treatment. By bathing is meant any number of processes commonly used to cleanse the body and face, e.g., showering. To be truly effective, these compositions must be such that an adequate level of benefit agent is retained on the skin after rinsing and/or towel drying without at the same time imparting an excessively oily feel to the wet and dry skin and without leaving it looking too shiny.

Bath oil, which is used by some consumers, must be applied sparingly because it does not absorb efficiently on the skin and the excess can be very oily and messy. Furthermore light bath oils (i.e., oils that have a low viscosity and spread on the skin) absorb more rapidly to overcome this problem, but are not very effective in providing longer lasting benefits.

Conventional oil-in-water emulsion type skin lotions or creams that are designed to be applied to dry skin, even water resistant variants, are very poorly retained when applied to wet skin that is either further rinsed or towel dried. By contrast, conventional water-in-oil skin lotions that are designed for application to dry skin are very efficiently retained on wet skin but are excessively greasy and messy and are not perceived to absorb quickly.

U.S. Pat. No. 5,578,299 to Starch and U.S. Pat. No. 5,928,632 are directed to gelled mineral oil compositions wherein the mineral oil is gelled by a specific oil soluble copolymers (ethylene/propylene/styrene/ and butylene/ethylene/styrene). No mention is made of structured oils wherein the structurant forms a network of finely divided solids, nor the criticality of the rheological properties of such networks, or of the droplet size. Also there is no mention of structured oils comprising a dispersed phase.

Further, the compositions described in U.S. Pat. No. 5,578,299 to Starch and U.S. Pat. No. 5,928,632 although they deposit on skin, are still perceived as greasy.

U.S. Pat. No. 5,661,189 to Grieveson et al is directed to an aqueous cleansing and moisturizing composition containing a dispersion of a thickened benefit agent. No mention is made of the criticality that the composition should have a mildness index as measured by the zein solubility test below a specific value (essentially equal to water). Furthermore, there is no mention that the compositions of U.S. Pat. No. 5,661,189 must have a foam generation index below a critical value as measured by the shake test (essentially non-foaming), and no mention that the thickening agents must be limited to structurants that specifically form a network of finely divided solids having the properties defined herein.

Finally, applicants have filed an application also entitled "Wet-Skin Treatment Compositions" on May 17, 2001, U.S. Ser. No. 09/859,862. This reference does not specifically disclose, as does the subject application, that structured oil phase also comprises a dispersed phase inside the structured oil phase.

There remains a need for compositions that can be applied to wet skin, absorb quickly and are perceived to be effective skin treatments and provide natural looking and natural feeling skin.

One objective of the current invention is to provide a composition in which the benefit agent efficiently deposits on wet-skin and is retained to a high degree when the skin is subsequently rinsed and dried.

A further objective is to provide a composition in which the oil phase is perceived to rapidly absorb when the composition is applied and rubbed on the wet skin.

A further objective is to provide a composition that is perceived to moisturize and protect the skin while still being perceived to leave the skin clean and with a natural look and a moisturized feel.

A still further objective of the present invention is to provide a convenient method to moisturize and treat the skin to yield an enduring effect that can be accomplished conveniently and routinely in a single step as part of the bathing process. Such a process will obviate the need for separate treatments.

Applicants have found that these and other objectives can be realized through the use of oil-in-water compositions in which the oil phase is specifically structured through a network comprising finely divided solid particle and the structured phase and the composition posses specific functional properties according to the tests described herein. Moreover, the structured oil phase comprises a dispersed phase comprising inorganic particles, organic particles and/or droplets of water-soluble ingredients.

BRIEF DESCRIPTION OF THE INVENTION

The subject invention provides skin care treatment compositions that are designed for use during bathing comprising an aqueous dispersion of one or more water-insoluble skin compatible oils which is structured by a stable network of finely divided solid particles and which structured oil phase comprises a dispersed phase. Provided the composition meets specific requirements in the tests set forth herein, the applicants have obtained compositions that are perceived to absorb quickly on wet skin, and impart their benefits while leaving the skin feeling non-greasy/oily after rinsing and/or drying.

More specifically, the invention provides a wet-skin treatment composition, comprising:

a) an aqueous phase comprising water and a dispersion stabilizer;

b) a structured oil phase comprising:

i) a liquid, skin compatible oil;
ii) a structurant that forms a stable network of finely divided solids in said liquid skin compatible oil at a temperature below 35° C. and wherein said structurant is present in an amount sufficient to cause said oil phase to have a viscosity of 100 to 5000 poise measured at 1 sec-1 at 25° C.; and
iii) a dispersed phase (preferably comprising about 1-40% of the structured oil phase) within the structured oil phase;

wherein said dispersion-containing oil phase is itself dispersed and stabilized in said aqueous phase to form an oil-in-water emulsion having a weight average droplet size of 1-500 microns and the weight average drop size of the structured oil is at least 10 times larger than the size of particles dispersed inside the structured oil;

wherein said structured oil phase is capable of being efficiently retained on the skin upon rinsing as measured by a Skin Retention Efficiency Index of at least 0.15 as determined in the In-Vitro Skin Retention Test, wherein said wet skin treatment composition has a Zein Solubility below 0.3 as measured by the Zein Solubility Test, and a Foam Volume below 5 cc as measured in the Solution Shake Test.

DETAILED DESCRIPTION OF THE INVENTION

The inventive composition described herein is designed for use as part of the bathing process to essentially treat the skin after it has been cleansed but while it is wet. To be of most utility, the composition should behave in an optimal fashion when it is used. Firstly the composition should be capable of depositing its beneficial ingredients quickly on the wet skin after the composition is applied. The beneficial agents should only deposit on the skin during active rubbing or there is a chance it will cause a slipping hazard. Secondly, the beneficial agents should be such that it is perceived to be quickly absorbed by the wet skin much like a conventional lotion is perceived to absorb on dry skin following rubout. Thirdly, the benefit agents should be substantively retained on the skin following further rinsing as would occur by a consumer rinsing off excess material, or casual exposure to the shower stream. Finally, the composition should confer desirable benefits to the skin that last longer than a few minutes while providing a clean and non-greasy/oily feel and appearance after bathing.

It should be understood that the terms "substantial retention" and "non-greasy/oily feel" are somewhat relative variables because they are subject to the variability of human preference. For example, some consumers, especially those with dry skin, appreciate a highly unctuous skin feel while others have an aversion to any perception of oiliness (oily skin consumers). Furthermore, the optimum level of material retention and skin lubricity are also dependent on skin color and overall skin condition. Consequently it is not practical and in fact not desirable to place overdue limitations on retention and lubricity because the compositions of this invention are desirably tailored to meet the needs and preferences of different types of consumers. Not withstanding this limitation, it is desirable that the compositions are capable of efficient delivery of benefit agents to the skin.

It is possible to achieve the optimal behavior described above with a composition employing specific aqueous dispersions of structured oils that meet specific functional criteria.

The elements of the invention and their functional properties are described in more detail below.

Aqueous Phase

The aqueous phase generally comprises 50 to about 97 wt. % of the composition and can be predominantly water. The aqueous phase is the continuous phase of the instant composition in which the structured oil phase (and dispersed phase within) is dispersed. The aqueous phase contains the dispersion stabilizer (discussed below), and optionally such ingredients as preservatives, wetting agents, auxiliary emulsifiers and various optional benefit agents (see below)

A Structured Oil Phase

The structured oil phase of the subject invention comprises three essential components: a skin compatible oil, a structurant that can form a stable network at a temperature below 35° C., and dispersed phase within the structured oil phase.

As noted, the structured oil phase has a dispersed phase. This dispersed phase contains solid particles or water soluble skin benefit agent to enhance the retention of solid particles or water soluble ingredients on the skin from an in-shower skin conditioner.

Skin Compatible Oils

A skin compatible oils is defined here as an oil that is liquid at the temperature at which bathing is carried out that is deemed safe for use in cosmetics being either inert to the skin or actually beneficial. The most useful skin compatible oils for the present invention include ester oils, hydrocarbon oils, and silicone oils.

Ester oils as the name implies have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

A second type of useful esters oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives, provided they are liquids. Proprietary ester blends such as those sold by Finetex as Finsolv® are also suitable, as is ethylhexanoic acid glyceride.

A third type of ester oil is liquid polyester formed from the reaction of a dicarboxylic acid and a diol. An example of polyesters suitable for the present invention is the polyesters marketed by ExxonMobil under the trade name PURESYN ESTER®.

A second class of skin compatible oils suitable for the present invention is liquid hydrocarbons. These include linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Light (low viscosity) highly branched hydrocarbon oils are also suitable.

Petrolatum is a unique hydrocarbon material and a useful component of the present invention. Since it is only partially comprised of a liquid fraction at room temperature, it is more properly regarded as either the "structured oil phase" when present by itself or alternatively as the "structurant" (see below) when admixed with other skin compatible oils.

A third class of useful skin compatible oils is silicone based. They include linear and cyclic polydimethyl siloxane, organo functional silicones (alkyl and alkyl aryl), and amino silicones.

Structurant

Another component of the structured oil phase is a structurant. The structurant must satisfy two requirements.

Firstly, the structurant must be capable of forming a stable network of finely divided solids in the skin compatible oil phase at a temperature below 35° C. This property is critical so that the structured oil is active during use but is not perceived as gritty. By finely divided solids is meant a network comprised of particles of a weight average size predominantly below about 25 microns, preferably below 10 microns and most preferably below 1 micron. By stable, is meant the network survives at least one month of storage at 25° C. and 35° C.

The structurant provides structured oil phase with the correct rhelogical properties. To provide effective deposition and retention to the skin, the structured oil phase should have a viscosity in the range of 100 to 5000 poise measured at 1 Sec-1, preferably 200–3000 poise, and most preferably 200–2000 poise as determined by Haake rotational viscometer utilizing concentric cylinders.

It is also desirable for the oil phase be pseudoplastic, i.e., to have shear thinning behavior to facilitate an elegant rub-in of the oil phase after it deposits on skin. Thus especially preferred stucturants are those that can meet the above requirements and also produce a structured oil phases that has a viscosity in the range of 30–200 poise measured at 10 sec-1, preferably 40–150 poise at 10 sec-1 measured with Haake viscometer as noted above.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and be retained after rinsing and drying to provide long-lasting after wash skin benefit without causing a too oily/greasy wet and dry feel. It is believed that the highly desirable in-use and after-use properties of the such structured oils are due to their shear thinning rheological properties and the weak structure of the network. Due to its high low-shear viscosity, the solid-network structured oil can stick and retain well on the skin during application of the skin conditioner. After being deposited on the skin, the network yields easily during rubbing due to the weak structuring of the crystal network and its lower high-shear viscosity.

The structurant can be either an organic or inorganic structurant. Preferred inorganic structurants are hydrophobically modified silica or hydrophobically modified clay with particle size less than 1 micrometer. Examples are Bentone 27V, Bentone 38V or Bentone gel MIO V from Rheox, and Cab-O-Sil TS720 or Cab-O-Sil M5 from Cabot Corporation.

The organic structurants are either crystalline solids or amorphous gels with molecular weight less than 5,000 Daltons, preferably less than 3,000 Daltons.

Preferred organic structurants have a melting point greater than 35° C., preferably greater than 40° C. Especially preferred structurants are those that can form a solution with the selected skin compatible oil at a temperature higher than their melting point to form a free flowing clear solution. Upon cooling to the ambient temperature, the organic structurant precipitate from the oil phase to form a 3-dimensional crystal structure providing the physical properties set forth above.

Examples of organic thickeners suitable for the invention are solid fatty acid esters, natural or modified fats, fatty acid, fatty amine, fatty alcohol, natural and synthetic waxes, and petrolatum. Petrolatum is a preferred organic structuring agent.

Particularly preferred organic structurants are solid fatty acid esters and petrolatum. Examples of solid fatty esters are mono, di or tri glycerides derivatives of palmitic acid, stearic acid, or hydroxystearic acid; sugar fatty ester or fatty esters of dextrin. Examples of these polyol fatty acid esters are described in U.S. Pat. Nos. 5,427,704, 5,472,728, 6,156,369, 5,490,995 and EP patent 398409 incorporated by reference herein. Trihydroxystearin sold under the trade name of THIXCIN R from Rheox Corporation is found particularly useful for structuring triglyceride ester oils.

The level of structurant present in the structured oil phase can be in the range of 1 to 90% and depends on the type of structurant used and the nature of the skin compatible oil. For solid organic structurants such as trihydroxystearin, the preferred level is 3 to 15%. However, the exact levels used should provide a stable network having the desired viscosity in the range of 100 to 5000 poise measured at a shear rate of 1 Sec-1 and can be readily optimized by one skilled in the art.

The structured oil phase comprising the skin compatible oil(s) and the structurant(s) described above are dispersed in the aqueous phase to form droplets that have a weight average droplet diameter that is in the range of 10–1000 microns, preferably 20–1000, more preferably 50–500 microns.

A third component of the structured oil is a dispersed phase which is contained within the structured oil. The dispersed phase found within the structured oil may comprise inorganic particles, organic particles and/or droplets of water-soluble ingredients.

Examples of inorganic particles include but are not limited to unmodified or modified silica, talc and mica; and examples of organic particles are silicone powders or capsules such as perfume capsules or vitamin E capsules. These solid particles should preferably be cosmetic grade approved for personal cleansing application. Preferred solid particles are cosmetic grade solid particles that are widely used in skin lotions or color cosmetics to improve either the tactile or visual appearance of the skin.

Capsules suitable for this invention are free flow powders prepared by various encapsulation processes such as interfacial polymerization encapsulation, coacervation encapsulation, spray drying/cooling encapsulation or spray coating encapsulation. Water-soluble ingredients which may be used include skin benefit agents used to improve the state of the skin include (a) humectants used to retain water in the skin such as glycerol, sorbitol, glycols, polyols, urea, water soluble polymers and their mixtures; (b) lipid barrier repair agents that are useful for strengthening, and replenishing the stratum corneum's barrier lipids such as cholesterol, cholesterol esters, ceramides, and pseudoceramides; (c) vitamins used to strengthen the skin such as vitamin A, B, and E and vitamin alkyl esters, including vitamin C alkyl esters; and (d) anti-aging agents used to exfoliate and stimulate cell turnover such as $\alpha$ and $\beta$ hydroxy acids, retinol, and retinol esters.

Structured oil containing the dispersed phase can be prepared by mixing the dispersed phase together with the structured oil before adding it to the aqueous phase. To improve the stability of the dispersed phase in the oil during mixing or after preparation, water-in-oil emulsifiers such as ABIL EM90 from Goldschmidt Chemical or Arlacel 80 or Arlacel 186 from Uniqema can be used. Typically the dispersed phase in the structured oil will have size of 0.1 to 150 microns, preferably 0.2 to 100 microns.

The dispersed phase is present in the structured oil phase at a level of 0.01-45%, preferably 0.5 to 42%, more preferably 1 to 40% of the structured oil phase.

Generally the structured oil phase (containing dispersed phase) is present in the wet-skin treatment composition at a level of 3 wt. % to about 50 wt. %, preferably from 4 wt. % to about 35 wt. %, and most preferably from 5 wt. % to about 25 wt. %.

Dispersion Stabilizer

Another required element of the invention is an emulsion stabilizer (found in aqueous phase). The dispersion stabilizer must provide adequate storage stability to the composition. Since the structured oil phase has a weight average droplet size that is greater than 10 microns, typically in the range of 50 to 500 microns, it is prone to separate under the action of gravity (creaming or sedimentation depending upon its density). The structured oil phases of this invention are also prone to stick together and coalesce. Without being bound by theory, it is believed that the stable solid network facilitates coalescence by providing asperities that induce film rupture. The same property that is useful in achieving efficient deposition on skin also makes the structured phase prone to instability on storage.

The most effective dispersion stabilizers are consequently those that can provide an adequate structure to the aqueous phase to immobilize the droplets thus preventing both gravitational separation and collision with other droplets. However, if the dispersion is too stable, the droplets of structured oil are inhibited from coming into proximity with the skin and thus effectively depositing. Therefore, the most effective dispersion stabilizers provided have excellent stability in the bottle but loose their effectiveness in immobilizing the structured oil when they are applied to wet skin.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provides physical stability of the large structured oil droplets, in the surfactant composition at 40° C. for over four weeks.

Inorganic dispersion stabilizers suitable for the invention includes, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizer are defined here as organic molecules that have a molecular weight generally lower than 1000 Daltons and form a network in the aqueous phase that immobilizes the dispersed structured oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carton atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizers is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum.

An especially preferred types of polymeric dispersion stabilizer agent include acrylate containing homo and copolymers. Examples include the crosslinked poly acrylates sold by B. F. Goodrich under the CARBOPOL trade name; the hydrophobically modified cross linked polyacrylates sold by B. F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

Auxiliary Benefit Agents

The composition can optionally contain a variety of auxiliary agents. These auxiliary agents: functional skin benefit agents; sensory modifiers; and miscellaneous ingredients such as essential oils, and preservatives.

Functional Skin Benefit Agents

These materials function to in some way improve the state of the skin and include the following:

a) humectants used to retain water in the skin such as glycerol, sorbitiol, glycols, polyols, urea and their mixtures;

b) lipid barrier repair agents that are useful for strengthening, and replenishing the stratum corneum's barrier lipids such as cholesterol, cholesterol esters, ceramides, and pseudoceramides;

c) additional occlusive agents used to hold water in the stratum corneum such as natural and synthetic waxes and polyethylene;

d) vitamins used to strengthen the skin such as vitamin A, B, and E and vitamin alkyl esters, including vitamin C alkyl esters;

e) anti-aging agents used to exfoliate and stimulate cell turnover such as $\alpha$ and $\beta$ hydroxy acids, retinol, and retinol esters;

f) Sunscreens such block the suns harmful UV rays such as octyl methoxy cinnamate (Parsol MCX) and butyl methoxy benzoylmethane (Parsol 1789), ultra-fine TiO2, ZnO and their mixtures;

g) skin lightening agents used to increase the lightness on the skin such as niacinamide;

h) antimicrobial agents such as 2-hydroxy-4,2',4'-trichlorodiphenylether (Triclosan or Ergasan DP300) and 3,4,4'-trichlorocarbanilide (TCC);

i) antioxidants used to reduce photodamage and premature damage due to excessive oxidation such as ascorby palmitate, Vitamin E acetate, butylated hydroxyanisole and; 2,6-ditertiarybutylpara-cresol;

j) insect repellants such as N,N-dimethy-m-toluamide, 3-(N-butyl-Nacetyl)-aminopropionic acid, ethyl ester and dipropyl isocinchomeronate.

mixtures of any of the foregoing components.

Sensory Modifiers

These materials improve the aesthetic properties of the formulation and can be mixed with the structured oil phase before adding it into the aqueous phase or can be added to the aqueous phase to form a solution or dispersion. Suitable sensory modifiers include:

a') emollient oils and emollient waxes used to improve the feel of the composition after rubbing into the skin, including: silicone resins, natural and synthetic waxes such as carnauba, spermaceti, beeswax, lanolin and derivatives thereof; higher fatty acids and alcohol;

b') skin conditioning polymers that can alter the wet and dry skin feel provided by the composition. Such polymers include non-ionic polymers such as polyethylene oxide, polyvinyl alcohol, polyvinyl pyrrollidone, anionic polymers such as polyaspartate, poly maleates and sulfonates, cationic polymers and their mixtures. Suitable cationic polymers include Guar hydroxypropyltrimonium chloride, Quaternium-19, -23, -40, -57, poly(dimethyldiallylammonium chloride), poly (dimethyl butenyl ammonium chloride)-, w-bis (triethanolammonium chloride), poly (dipropyldiallylammonium chloride), poly (methyl-beta propaniodiallylammonium chloride), poly (diallylpiperidinium chloride), poly (vinyl pyridinium chloride), quaternised poly (vinyl alcohol), quaternized poly (dimethylaminoethylmethacrylate), and water insoluble polymers especially useful to modify wet skin feel such as polybutene, polyisobutene, polyisoprene, polybutadiene, polyalphaolefin and polyesters; and mixtures thereof;

c') perfumes used to provide in-use fragrance and lingering fragrance on skin;

d') distributing agents (also called a wetting agents) used to help the wet-skin treatment composition spread easily and uniformly over the body and reduce drag such as alkyl betaines, nonionic surfactants, silicone surfactants, and high molecular weight polyethene oxide;

e') Emulsifying and dispersing agents that can reduce interfacial especially useful during processing. Some exemplary materials include: alkyl glycosides, other nonionic, cationic, and zwitterionic surfactants;

f') chemosensory used to provide pleasant sensations like cooling such menthol and its derivatives, and certain essential oils well known in the art; and g') cosmetic grade solid particles that are effective in affecting either tactile or visual appearance of the skin such as talc, TiO2, silica or mica; for visual effect, color cosmetic grade pigments such as Timiron® MP pigments or Timiron® Splendid interference pigments are particular useful.

The sensory modifier of g' are actually part of the dispersion incorporated into the structured oil phase.

Miscellaneous Agents

The composition of the invention can also contain a various essential oils such as, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, Citronella, borneol, linalool, geraniol, evening primrose, thymol, spirantol, pinene, limonene and terpenoid oils.

Further useful classes of materials are preservatives, chelating agents and antioxidants. These materials are especially important when triglyceride ester oil are employed. Suitable preservatives for the present composition include: dimethyloldimethylhydantoin (Glydant XL1000), parabens, sorbic acid etc. Suitable chelators include tetrasodium ethylenediaminetetraacetate (EDTA) sold under the trade name VERSENE® 100XL, and hydroxyethilidene diphosphonic acid sold under the trade name Dequest® 2010 or mixtures in an amount of 0.01 to 1%, preferably 0.01 to 0.05%. An example of an antioxidant is butylated hydroxytoluene (BHT). Chelating agents are useful in binding metal ions including Ca/Mg as well as transition metal ions.

Still other useful agents include organic solvents, such as ethanol; auxiliary thickeners, coloring agents, opacifiers and pearlizers such as zinc stearate, magnesium stearate, $TiO_2$, EGMS (ethylene glycol monostearate) or Lytron® 621 (Styrene/Acrylate copolymer); all of which are useful in enhancing the appearance or cosmetic properties of the product.

The compositions described above are meant to be applied to wet-skin as a penultimate step or one of the last steps in the bathing process. They are also meant to leave a significant portion of their beneficial agents in contact with the skin. To be most effective in this regard the compositions should satisfy three additional requirements.

The first additional requirement is that the composition should be extremely mild to the skin and should not have any harsh surfactants present, which have the potential to be retained and irritate the skin if not completely rinsed. This requirement can be met by ensuring that the composition be below a critical value in a test that correlates with the mildness of an aqueous composition. Such a test is the Zein Solubility Test (described in the Methods Section below) that is well known in the art as a rapid screen for the irritation potential of a composition especially one that contains surface active materials (W. Kastner and P. J Frosh, *skin irritation of various anionic surfactants in the duhring-chamber-test on volunteers in comparison with in-vitro and animal test methods*, Fette Seifen Anstrichhmittel Volume 83, Pages 33–46 (1981)). Thus, the wet-skin compositions suitable for the present use must have a Mildness Index less than 0.3 wt. % and preferably less than 0.1 wt. % as measured by the Zein Solubility Test: a value that is essentially close to the Zein solubility of pure water, about 0.04 to 0.06 wt. %.

The second additional requirement is that the compositions be essentially non-foaming. The reason for this requirement is related to human behavior based on experience. Although the treatment compositions described herein are highly substantive, it is important to minimize how vigorously (time and mechanical action) the skin is rinsed before bathing is concluded. Foam is a cue that foreign detergent has been applied to the skin and must be removed via vigorous rinsing otherwise it will be left behind. Thus, the wet-skin treatment compositions described herein should have a Foaming Volume of less than 5 CC, preferably less than 2 CC and most preferably less than 1 CC when measured by the Solution Shake Test described below in the Methods Section below.

The last additional requirement is that the wet-skin treatment composition actually deposits sufficient material on the wet skin to be effective and that this deposited material be retained after rinsing and or towel drying. The method used to measure the ability of the composition to be retained on the skin during rinsing is the In-vitro Skin Retention Test described in the Methods Section. Thus, to be an effective wet skin treatment, the composition should have a Skin Retention Index of at least 0.15, preferably greater than 0.25 and most preferably greater than 0.5.

Test Methods

This section describes the test methods that are used to characterize the wet-skin compositions especially with respect to their irritation potential, Zein Solubility Test (Irritation Potential)

The Zein solubility test provided a rapid and convenient screen for irritation potential especially for compositions that contain surface active agents. The procedure is as follows:

1. Mix 5 g. of the cleanser with 45 g of deionized water using a magnetic stirrer for 5 to 10 minutes to form an uniform solution.
2. Record the pH of the solution.
3. Withdraw about 5 ml of the solution and filter it through 0.45 micrometer filter into a vial for % solid measurement (mark the solution as blank).
4. Add about 2 g of zein to the remaining solution and mix for 60 minutes using a magnetic stirrer. Check the solution every ten minutes to ensure that there is enough undissolved zein in the mixture. If most of the zein dissolved, add 1 more gram of zein into the solution and continue the mixing (always keep zein in excess but not too much because zein will swells and make the solution difficult to filter).
5. After mixing, let the solution settle for 5 minutes. Withdraw 5 ml of the supernatant in a syringe and filter it through 0.45 micron filter into a vial and mark it as sample. (Centrifuge the solution at 3,000 rpm for 5 minutes before filtration if the supernatant is hard to separate).
6. Determine the % solid of the blank and the sample by weighing about 3 to 4 grams of the filtrate in an aluminum dish using an analytical balance and drying the filtrate overnight in a 75° C. oven.
7. Calculate % solid of zein dissolved in the diluted liquid solution using the following equation.

% solid of zein solubilised=% solid of sample−% solid of blank

Solution Shake Test (Foaming)

This test provided a simple an convenient measure of the ability of the composition to form foam. The test method is as follows:

1. Mix 2 g of the conditioner with 18 g of deionized water for about 2 to 3 minutes until it forms an uniform solution.
2. Add 10 cc of the above diluted conditioner solution to a 50 cc cylinder (15 cm high, 2.06 cm in diameter).
3. Grape the top of the cylinder and sake the cylinder in a up and down motion 30 times within 8 to 12 seconds.
4. Once shaking is over, wait 60 seconds before taking the foam measurement.
5. Measure the foam volume, which is defined as the volume from the surface of the solution to the top of the foam column.
6. Duplicate the run and take the average as the foam volume of a specific product.

The following compositions are used for reference:

| Composition | Shaker Test Foam Volume (CC Foam) |
| --- | --- |
| Dove All-Day Moisturizing Body Wash | 26 |
| Oil of Olay Daily Renewal Moisturizing Body Wash | 29 |
| Lever 2000 Pure Rain Body Wash | 43 |

In-Vitro Skin Retention Test

This in-vitro test simulates the ability of the composition when applied to clean wet skin to be retained after rinsing with water and drying with a towel. To accomplish this procedure a UV chromophore, Parsol MCX is incorporated into the oil phase of test compositions and used as the detection probe.

The test procedure is as follows:

Substrate Preparation

A sample of porcine skin (3 to 4 weeks old female) used as the substrate is washed with 15% NaLES (sodium ethoxy (3 EO) sulfate) solution, rinsed with tap water, patted dry and shaved. The skin is cut into pieces approximately 4 cm by 9 cm and stored in the freezer for later use.

Test Procedure

1. A 4×9 cm sample of skin as prepared above is washed with 0.2 to 0.3 grams of a 15% NaLES solution for 30 seconds and rinsed with warm tap water for 30 seconds.
2. A calculated amount of shower conditioner (at a dose of 3 micrograms per square centimeters) is applied and rubbed in a circular motion on the skin for 30 seconds.
3. The skin is then rinsed with tap water for 30 seconds at a flow rate delivering 13.5 g to 13.8 g of water per second at a temperature of 30° C.
4. The skin is patted dry with a paper towel and then left to air-dry for 5 minutes.
5. A glass ring of 3 cm in diameter is placed tightly on the skin.
6. With a mechanical pipette 5 mL of heptane are dispensed into the ring while holding the ring tautly.
7. The heptane is mixed on the skin with a transfer pipette by slowly squeezing the pipette repeatedly for 2 minutes and 30 seconds.
8. After 2 minutes and 30 seconds are up, the heptane is transferred from the ring to a small capped vial.
9. Steps 7–9 are repeated. There should be in total of approximately 10 mL of heptane in the small vial.
10. The vial is weighed and labeled.
11. The Parsol MCX concentration in the heptane extract are determined with a UV spectrometer (Biorad GS 700) using a 1 cm cell and a wavelength 900 to 1900 Nm.
12. The amount of Parsol MCX extracted per $cm^2$ of porcine skin is then calculated as follows:

MCX extracted per $cm^2$=Wt. % MCX in heptane×Total Wt heptane extracted÷7 $cm^2$ 13. The percent of oil retained on the skin is finally calculated using the following equation and recorded as % retention of oil after rinsing.

$$\text{Oil Retention Index} = \frac{\text{Amount of Parsol } MCX \text{ extracted per cm}^2 \text{ of porcine skin}}{\text{Amount of Parsol } MCX \text{ dosed per cm}^2 \text{ of porcine skin}}$$

Expert Sensory Panel Evaluation

This evaluation protocol is used to evaluate the sensory properties of the wet-skin treatment compositions and employs an expert sensory panel. The methodology is a variant of that initially proposed Tragon and employs a language generation step.

The procedure is as follows:
1. wet hands and forearms under running water for 5 seconds.
2. grab the soap bar, wet under running water, and generate lather by rotating the bar 5 times in hand.
3. put the bar back, apply the lather on the forearm and wash the forearm for 5 seconds.
4. rinse the hands
5. rinse the forearm under the running tap water for 5 seconds.
6. dispense 0.5 cc product on the forearm from a syringe.
7. rub the product all over the forearm for 10 seconds.
8. use the hand to help rinse the forearm under running water for 7 seconds. (evaluate product's rinsing properties and wet-skin feel)
9. pat dry the hands and the forearm. (evaluate product's skin feel right after and 15 to 20 minutes after pat dry)

The key attributes evaluated and its definition are summarized as follows.

| Key Attributes | Definition of Attributes |
|---|---|
| OILY/GREASY (TOUCH) | Perception of a slippery substance, light and slick (oily) to heavy and thick (greasy) |
| WAXY COATING | A smooth film with slight hesitation when move the fingers across the skin |
| RINSEABILITY | Ease of rinse off the product |
| TACKY/STICKY | Resistance/adhesive quality to the skin after product usage |
| DRAG | The ability of moving fingers across the skin. (Low drag to high drag) |
| HYDRATED/MOISTURIZED | A feeling of moisture being absorbed into skin, skin not dry. |
| SOFT | Skin surface that yields easily to finger pressure |
| SMOOTH | Ease with which the fingers glide across the surface of the skin |
| AMOUNT OF RESIDUAL | A feeling of product remaining on the surface of skin. |

The water used was 40 PPM hardness expressed as PPM $CaCO_3$.

Controlled Application Dryness Tests

Various controlled application clinical test methods have been developed to quantify the effects of cleansers on the skin, particularly to examine their relative potential to dry or moisturize the skin and their effects on skin barrier function. These tests can easily be adapted to wet-skin treatment compositions because such compositions are essentially rinse-off treatments and can be applied during testing in much the same way as cleansers apart from dosage and lather considerations. The tests utilize a combination of subjective evaluations (visual skin condition assessment by expert graders) as well as objective measures, i.e. instrumental biophysical measurements to quantitate treatment induced changes to the skin's barrier function and skin's ability to retain moisture. Several well known alternative techniques can be employed to visual asses dryness, moisturization, and barrier function using carefully controlled application protocols. These include the Leg Wash, the Arm Wash, and the Forearm Controlled Application Test protocol. These protocols are described below:

Modified Leg Wash Protocol

This protocol is used to examine the effect of wet-skin treatment compositions on improving leg dryness. Study design and procedures are as follows:

At least 15 female subjects (35–65 year old) are enrolled into the study and at least 13 must complete the product application phase. Dove® beauty bar was provided for general cleansing six days prior to the start of test product application. Subject's were instructed to continue the use of Dove for home cleansing throughout the study.

On the first day of product application, a template was used to divided the subjects' legs into a two 54 $cm^2$ sites (upper/lower). Two treatment sessions per day (morning, afternoon) were performed on days 1–2, and one wash session was performed in the morning on day 3. The washes and/or evaluations were scheduled approximately 4 hours apart.

The test product application procedure was as follows: The test site was first washed for 30 seconds with a standard mild cleansing solution and then rinsed for 15 seconds under running water. The wet-skin treatment composition (250 uL) was then immediately applied to the skin. The product was manipulated across the test site for 30 seconds, retained for 30 seconds, rinsed for 15-seconds, and patted dry. Study personnel performed all product applications.

Evaluation Methods

Baseline visual assessments are made prior to the start of the product application phase, and immediately before each treatment session to evaluate dryness and erythema thereafter. A test site will be discontinued if a clinical dryness or erythema score of >3.0 is reached, or at the subject's request. If only one leg is discontinued, the remaining leg will continue to be washed according to schedule. The same evaluator under conditions that are consistent throughout the study will conduct all of the visual evaluations. The 0–4 grading scale shown in Table 1 is used to assess the test sites for dryness and erythema. To maintain the evaluator's blindness to product assignment, the visual assessments will be conducted in a separate area away from the product application area.

Visual Dryness Grading—Leg Wash Application
(Same Scale Used in Modified Arm Wash Protocol)

| Grade | Dryness |
|---|---|
| 0 | None |
| 0.5 | Perceptible dryness, whiteness in lines of the skin (fine white lines) |
| 1.0 | Slight flaking/uplifting of flakes (patchy and/or powdered appearance. |
| 1.5 | Slight to moderate flaking/uplifting flakes (uniform). |
| 2.0 | Moderate flaking/uplifting flakes, (uniform) and/or slight scaling. |

-continued

| Grade | Dryness |
| --- | --- |
| 2.5 | Moderate to severe flaking/uplifting flakes and/or moderate scaling. |
| 3.0 | Severe flaking/scaling, uplifting of scales and/or slight fissuring |
| 3.5 | Severe scaling/uplifting scales and/or moderate fissuring |
| 4.0 | Severe scaling/uplifting scales; with severe fissuring/cracking |

Data Analysis

If product application has been discontinued on a test site due to a dryness or erythema score of ≧3.0 all data (clinical grades) at that evaluation for that subject are carried forward for the remaining time points. Data for the discontinued sites are used such that the last acceptable reading (i.e. the last fair comparison) is used as the endpoint in the analysis. Actual data for the discontinued sites is recorded, but not included in the statistical analysis.

The dryness and erythema scales are treated as ordered categorizations; hence, nonparametric statistical methods are used. At each evaluation point, the differences in clinical grades (evaluation score subtracting the baseline score) within each product is evaluated using the Wilcoxon Signed-Rank test, Pratt-Lehmann version (Lehmann, E. L. *Nonparametrics: Statistical Methods Based on Ranks*. San Francisco, Calif.: Holden Day, 1975, pg. 130). Statistical significance will be determined at the 90% confidence level ($p<0.10$). This will indicate if the treatment results are statistically significant from their baseline score.

Means, median scores, and mean ranks across all subjects for each treatment at each evaluation point are calculated and recorded. At each evaluation point, the differences in clinical grades (evaluation-baseline) for each test product is evaluated using the Wilcoxon Signed-Rank test, Pratt-Lehmann version. This indicates if the products are statistically significantly different from each other (90% confidence level ($p<0.10$).

For the instrumental data, the same comparisons are made using parametric statistical methods. The TEWL and conductance measurements are averaged separately for each subject, site, and session. For all treatments, treatment differences are statistically compared using a paired t-test at each evaluation point. Statistical significance will be determined at the 90% confidence level ($p<0.10$).

The data will also be assessed to determine whether one treatment impacts skin condition to a greater degree relative to the other test cell through the number of discontinuations. For each attribute, a survival analysis will examine treatment performance over wash sessions. The analysis will incorporate the number of wash sessions that a subject's treatment site is actually washed in the study. If the treatment site is discontinued, then the site's survival time is determined at that evaluation. An overlay plot of the estimated survival function for each treatment group will be examined. The Log-Rank test statistic will be computed to test for homogeneity of treatment groups. This test will tell if the survival functions are the same for each of the treatment groups. Also, the number of wash sessions survived by a treatment site during the study (prior to the possible discontinuation of that side) will be compared between treatments via a paired t-test, using the test subject as a block.

If dryness and erythema rank scores are also assigned at each evaluation, the treatments will be compared with respect to the rank scores by application of the Friedman's test on the ranks, with subject acting as a block [ref. Hollander, Myles and Douglas A. Wolfe. *Nonparametric Statistical Methods*. New York, N.Y. John Wiley & Sons, 1973, pp. 139–146].

At each evaluation, if Friedman's test examining treatment effects is significant at a p-value of 0.05 or other preselected level, then multiple comparison tests comparing each pair of treatments will be performed. For comparison of all possible pairs of treatments, the procedure documented in Hollander and Wolfe pp. 151–155 will be used. This test is based on the Friedman rank sums. For comparison of treatments vs. a control, the procedure documented in Hollander and Wolfe pp. 155–158 will be used.

Modified Standard Arm Wash Protocol

This test has been described in detail and validated by Sharko et al for cleansers and is easily adapted for rinse-off wet skin treatment compositions (*Arm wash evaluation with instrumental evaluation—A sensitive technique for differentiating the irritation potential of personal washing products*, J. Derm. Clin. Eval. Soc. 2, 19 (1991)). A description of the protocol follows:

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores ≦1.0 and erythema scores ≦0.5, and be free of cuts and abrasions on or near the test sites to be included in the product application phase. Subjects who qualify to enter the product application phase will be instructed to discontinue the use of the conditioning product and any other skin care products on their inner forearms, with the exception of the skin cleansing test formulations that are applied during the testing visits. During the five (5) day product application phase of the study, visual assessments for dryness and erythema are conducted prior to each wash session. Wash sessions are conducted 4 times daily, approximately 1.5 hours apart for the first four (4) days. On the last day, there are two (2) wash sessions followed by a final visual evaluation three hours after the final wash. Each application consists of a one application of the rinse-off treatment composition. Up to a total of 18 washes and 19 evaluations performed in this protocol. Instrument measurements are taken at baseline, at various time points after the application and rinsing phase.

Application Procedure:

1. Timer is set to designated application time
2. The left test site (volar forearm) is washed with a control cleanser (e.g., 1 minute), and rinsed with warm water (90°–100° F.).
3. Treatment product is dispensed, and the timer is started.
4. The site is treated in a back and forth motion, one stroke per second (a stroke is from the inner elbow to the wrist and back to the inner elbow) for the designated time.
5. The fingertips are re-wet at the midpoint of application, i.e., at 30 sec, for a one minute application.
6. The site is rinsed with warm running water and patted dry.
7. The above procedure (1–6) is repeated for the right test site.

Evaluation Methods

Baseline visual assessments are made prior to the start of the product application phase, and immediately before each wash session to evaluate dryness. The same evaluator under conditions that are consistent throughout the study will conduct all of the visual evaluations. The 0–4 grading scale that is essentially identical to that described for the Leg Wash Protocol above, shown in is used to assess the test sites for dryness. To maintain the evaluator's blindness to product assignment, the visual assessments will be conducted in a separate area away from the product application area.

Transepidermal Water Loss (TEWL) measurements for barrier integrity are made on each test site using a Servomed Evaporimeter EP1 and/or EP2 at the beginning (baseline value), and at various time points after product application, and at the end of the study. Two consecutive fifteen-second readings per test site are taken for each TEWL evaluation, following a thirty-second equilibration period. (See method description below)

Skin conductance is measured using a SKICON-200 instrument, with an MT-8C probe, and/or Capacitance is measured using a Corneometer, at the beginning (baseline value), and at the end of the product application phase or at the time of discontinuation (final value). These methods provide objective measures of stratum corneum hydration. Three consecutive readings per test site will be taken and averaged (See method description below)

Data Analysis

The dryness is treated as ordered categorizations; hence, nonparametric statistical methods are used. At each evaluation point, the differences in clinical grades (evaluation score subtracting the baseline score) within each product is evaluated using the Wilcoxon Signed-Rank test, Praft-Lehmann version (Lehmann, E. L. Nonparametrics: Statistical Methods Based on Ranks. San Francisco, Calif.: Holden Day, 1975, pg. 130). Statistical significance will be determined at the 90% confidence level (p<0.10). This will indicate if the treatment results are statistically significant from their baseline score.

Means, median scores, and mean ranks across all subjects for each treatment at each evaluation point are calculated and recorded. At each evaluation point, the differences in clinical grades (evaluation-baseline) for each test product is evaluated using the Wilcoxon Signed-Rank test, Pratt-Lehmann version. This indicates if the products are statistically significantly different from each other (90% confidence level (p<0.10).

For the instrumental data, the same comparisons are made using parametric statistical methods. The TEWL and conductance measurements are averaged separately for each subject, site, and session. For all treatments, treatment differences are statistically compared using a paired t-test at each evaluation point. Statistical significance will be determined at the 90% confidence level (p<0.10).

The data will also be assessed to determine whether one treatment impacts skin condition to a greater degree relative to the other test cell through the number of discontinuations. For each attribute, a survival analysis will examine treatment performance over wash sessions. The analysis will incorporate the number of wash sessions that a subject's treatment site is actually washed in the study.

If dryness rank scores are also assigned at each evaluation, the treatments will be compared with respect to the rank scores by application of the Friedman's test on the ranks, with subject acting as a block [ref. Hollander, Myles and Douglas A. Wolfe. *Nonparametric Statistical Methods*. New York, N.Y. John Wiley & Sons, 1973, pp. 139–146].

At each evaluation, if Friedman's test examining treatment effects is significant at a p-value of 0.05 or other preselected level, then multiple comparison tests comparing each pair of treatments will be performed. For comparison of all possible pairs of treatments, the procedure documented in Hollander and Wolfe pp. 151–155 will be used. This test is based on the Friedman rank sums. For comparison of treatments vs. a control, the procedure documented in Hollander and Wolfe pp. 155–158 will be used.

The Modified Arm Wash Protocol described above is also easily modified to utilize 4 sites (2 on each arm) instead of two.

Transepidermal Water Loss Test (TEWL)

The Derma Lab Model #CR 200001–140 was used to quantify the rates of transepidermal water loss following the procedures similar to those outlined by Murahata et al (*"The use of transepidermal water loss to measure and predict the irritation response to surfactants"* Int. J. Cos. Science 8, 225 (1986)). TEWL provides a quantitative measure of the integrity of the stratum corneum barrier function and the relative effect of cleansers.

The operating principle of the instrument is based on Fick's law where $$(1/A)(dm/dt) = -D(dp/dx)$$

where

A = area of the surface ($m^2$)

m = weight of transported water (g)

t = time (hr)

D = constant, 0.0877 g-1 h-1 (mm Hg)-1 related to the diffusion coefficient of water p = partial pressure of water vapor in air (mm Hg)

x = distance of the sensor from the skin surface (m)

The evaporation rate, dm/dt, is proportional to the partial pressure gradient, dp/dx. The evaporation rate can be determined by measuring the partial pressures at two points whose distance above the skin is different and known, and where these points are within a range of 15–20 mm above the skin surface.

The general clinical requirements are as follows:

1. All panelists are equilibrated for a minimum of fifteen minutes before measurements in a test room in which the temperature and relative humidity are controlled.

2. The test sites are measured or marked in such a way that pre and post treatment measurements can be taken at approximately the same place on the skin.

3. The probe is applied in such a way that the sensors are perpendicular to the test site, using a minimum of pressure.

Probe Calibration is achieved with a calibration set (No. 2110) which is supplied with the instrument. The kit must be housed in a thermo-insulated box to ensure an even temperature distribution around the instrument probe and calibration flask.

The three salt solution used for calibration are LiCl, [$MgNO_3$]$_2$, and $K_2SO_4$. Pre-weighed amounts of slat at high purity are supplied with the kit instrument. The solution concentrations are such that the three solutions provide a RH of ~11.2%, ~54.2%, and ~97% respectively at 21° C.

General use of the instrument is as follows:

1. For normal studies, instrument readings are taken with the selector switch set for 1–100 g/m2 h range 2. The protective cap is removed from the probe and the measuring head is placed so that the Teflon capsule is applied perpendicularly to the evaluation site ensuring that a minimum pressure is applied from the probe head. To minimize deviations of the zero point, the probe head should be held by the attached rubber-insulating stopper.

3. Subject equilibration time prior to prior to evaluation is 15 minutes in a temperature/humidity controlled room.
4. The probe is allowed to stabilize at the test site for a minimum of 30 seconds before data acquisition. When air drafts exist and barrier damage is high it is recommended to increase the stabilization time.
5. Data is acquired during the 15 seconds period following the stabilization time.

Skin Hydration Test

The Corneometer CM802PC (Courage & Khazaha, Kohl, Germany) is a device widely used in the cosmetic industry. It allows high frequency, alternating voltage electrical measurements of skin capacitance to be safely made via an electrode applied to the skin surface. The parameters measured have been found to vary with skin hydration. However, they may also vary with many other factors such as skin temperature, sweat gland activity, and the composition of any applied product. The Corneometer can only give directional changes in the water content of the upper stratum corneum under favorable circumstances but even here the quantitative interpretations may prove misleading.

A widely used alternative is the Skicon Skin conductance Meter (I.B.S. Co Ltd. Shizuoka-ken, Japan).

Panelist Requirements for either instrument are as follows:

1. Subjects should equilibrate to room conditions, which are maintained at a fixed temperature and relative humidity for a minimum of 15 minutes with their arms exposed. Air currents should be minimized.
2. Physical and psychological distractions should be minimized, e.g., talking and moving around.
3. Consumption during at least 1 hour before measurement of hot beverages or of any products containing caffeine should be avoided.
4. Panelists should avoid smoking for at least 30 minutes prior to measurements.

Operating Procedure

1. The probe should be lightly applied so as to cause minimum depression of the skin surface by the outer casing. The measuring surface is spring-loaded and thus the probe must be applied with sufficient pressure that the black cylinder disappears completely inside the outer casing.
2. The probe should be held perpendicular to the skin surface.
3. The operator should avoid contacting hairs on the measure site with the probe.
4. The probe should remain in contact with the skin until the instrument's signal beeper sounds (about 1 second) and then be removed. Subsequent measurements can be made immediately provided the probe surface is known to be clean.
5. A minimum of 3 individual measurements should be taken at separate points on the test area and averaged to represent the mean hydration of the site.
6. A dry paper tissue should be used to clean the probe between readings.

EXAMPLES

Example 1

Retention of Oil When the Dispersed Phase is a Structured Oil

This example illustrates that structuring the skin compatible oil with a network dramatically improves its ability to be retained on wet skin after rinsing. The example also illustrates the high efficiency of retention of the inventive composition compared to the use of baby oil—a conventional composition often applied to wet skin during bathing.

Four samples with composition given in Table 1 were prepared to show effect of oil viscosity on deposition efficiency. All the samples contain same amount of oils (15 wt. %) with droplet size in the range of 2 to 300 microns. Samples were prepared using the method described as follow. An oil premix containing all the emollient oils in the formulation (sunflower seed oil, Parsol MCX, petrolatum, polybutene or trihydroxystearin) is prepared by mixing the oils at 70 to 85° C. to form a clear uniform mixture. The oil mixture is then cooled below 40° C. to form a viscous oil mixture before adding into the formulation. In a separate mixer, a thickened aqueous solution containing water soluble polymer (Xanthan Gum or Carbopol), surfactants, glycerin, perfume and Glydant plus with a pH in the range of 6.5 to 7.0 was prepared. 15 parts of the oil premix was then injected into 85 parts of the thickened aqueous solution using a syringe. The aqueous solution containing lumps of oil mixture was then passed through a screen to make the final product containing large oil droplets with size in the range of 20 to 300 microns. Screen with openings of 200 micrometer is used for Examples 1B, 1C and 1D. Screen with openings of 1000 micrometer is used for Example 1A. Example 1A contains droplets of low viscosity oil, a mixture of sunflower seed oil and Parsol MCX with viscosity less than 200 centistokes at 1 rps. Examples 1B, 1C and 1D contain viscose oil with viscosity higher than 20,000 centistokes at 1 rps. The mixture of low viscosity oils (Parsol MCX and sunflower seed oil) is thickened either with trihydroxystearin (Example 1D) or with petrolatum (Example 1B and 1C). A comparative example (Comparative Example 1) contains neat sunflower seed oil mixed with Parsol MCX was also used for comparison.

TABLE 1

|  | Example 1A | Example 1B | Example 1C | Example 1D | Comparative Example 1 |
|---|---|---|---|---|---|
| Xanthan Gum Keltro CG-RD | 0.43 | 0.43 | — | — | — |
| Carbopol Pemulene TR1 | — | — | 0.43 | 0.43 | — |
| KOH | — | — | 0.24 | 0.24 | — |
| Sunflower seed oil (Triglyceride oil) | 11.25 | — | 4.5 | 12.6 | 90 |
| Petrolatum | — | 7.50 | 9.0 | — | — |
| Indopol H1500 Polybutene | — | 3.75 | — | — | — |

TABLE 1-continued

|  | Example 1A | Example 1B | Example 1C | Example 1D | Comparative Example 1 |
|---|---|---|---|---|---|
| Thixcin R (trihydroxystearin) | — | — | — | 0.9 | — |
| Parsol MCX | 3.75 | 3.75 | 1.5 | 1.5 | 10 |
| Na Laureth (3) sulfate | 0.9 | 0.9 | — | — | — |
| Na cocoamidopropyl betaine | 0.45 | 0.45 | — | — | — |
| Alkyl polyglucoside Plantarem 2000 | — | — | 0.85 | 0.85 | — |
| Glycerin | 5.0 | 5.0 | 4.3 | 4.3 | — |
| Perfume | 0.5 | 0.5 | 0.34 | 0.34 | — |
| Glydant plux | 0.2 | 0.2 | 0.17 | 0.17 | — |
| DI water | To 100 | To 100 | To 100 | To 100 | 0.00 |
| Oil Viscosity (Poise) @ 1 Sec −1 | 0.15 | 380 | 560 | 1800 | 0.15 |
| Skin Retention Efficiency Index (after rinsing based on Parsol MCX) | 0.0343 | 0.644 | 0.377 | 0.455 | 0.12 | pH: 6.5 to 7.0

Deposition efficiency of these samples determined using the method described in the deposition protocol section is summarized in the table above. The result clearly show that oil retention of the wet-skin treatment composition provide a greatly enhanced retention when the oil phase is structured by a solid network and when the dispersed structure oil phase has the viscosity and droplet size set forth herein. In contrast unstructured oil phases (comprised of Parsol MCX or sunflower seed oil) even when at the correct droplet size are not efficiently deposited. Compare Samples 1B, 1C and 1D with Sample 1A. The skin retention efficiency for all the compositions containing large droplets of structured oil phase is higher than 0.35 and is more than a factor of 10 higher than the unstructured oil phase containing dispersion and is about a factor of 3 to 5 higher than the comparative example of baby oil—a widely used shower treatment.

Example 2
Effect of Particle Size of Structured Oil Phase on Oil Retention

This example illustrates the skin retention of wet-skin treatment compositions whose dispersed phase falls within the preferred particle size range.

Four samples with the composition same as Example 1B of Example 1 but having different particle sizes were prepared to show the effect of particle size on oil retention after rinsing. The particle size was measured using Malvern Mastersizer X. Effect of droplet size on oil retention is summarized at the table below. Particle size has a big effect on oil retention of viscous oil droplets. To achieve highest skin retention efficiency, the structured oil phase of the wet-skin treatment composition should have an oil droplets size that is larger than 1 micron, preferably larger than 5 microns.

TABLE 2

|  | Example 2A | Example 2B | Example 2C | Example 2C | Example 2D |
|---|---|---|---|---|---|
| Particle size (micrometers) | 0.243 um** | 4.59 um | 22.6 um | 189.6 um | 399.9 um |
| Oil retention index after rinsing based on Parsol MCX | 0.0216 | 0.214 | 0.54 | 0.61 | 0.71 |

**This sample contains submicron particles of 90% sunflower seed oil/10% Parsol MCX Example 3
Effect of Oil Viscosity and Composition on Perceived Sensory Properties This example demonstrates an important property of the wet-skin compositions employing structured oil technology disclosed herein. Namely, this technology is perceived to moisturize skin without imparting an excessively greasy/oil feel.

Three examples exemplifying the compositions of the instant invention were prepared having the compositions shown in Table 3. Example 3A and 3B respectively contain 7.5% and 15% of sunflower seed structured with Thixcin R. Example 3C contain 7.5% of sunflower seed oil structured with petrolatum, fatty acid and Superhartolan. 2 comparative examples and one commercial shower conditioner are used for comparison. Comparative Example 3D is a composition containing 7.5% of non-structured sunflower seed oil; and the comparative Example 3E is a control sample does not contain any oil but is otherwise identical to the other Example 3 compositions. All the compositions were prepared using the method described in Example 1.

feel 15 to 20 minutes after drying was perceived to have very oily/greasy wet-skin feel and to be difficult to rinse. In contrast, Example 3B provide a higher level moisturizing benefit but was easy to rinse and did not feel excessively oily/greasy.

TABLE 3

|  | Example 3A | Example 3B | Example 3C | Comparative Example 3D | Comparative Example 3E |
|---|---|---|---|---|---|
| Carbopol Pemulene TR1 | 0.46 | 0.43 | 0.46 | 0.46 | 0.46 |
| KOH | 0.24 | 0.22 | 0.24 | 0.24 | 0.24 |
| Alkyl polyglucoside Plantarem 2000 | 0.925 | 0.925 | 0.85 | 0.925 | 0.925 |
| Glycerin | 5.55 | 4.3 | 5.55 | 5.55 | 5.55 |
| Perfume | 0.37 | 0.34 | 0.37 | 0.37 | 0.37 |
| Glydant plux | 0.18 | 0.18 | 0.17 | 0.18 | 0.18 |
| DI water | 84.7 | 78.6 | 84.7 | 84.7 | 92.5 |
| Sunflower seed oil | 7.13 | 14.25 | 2.25 | 7.5 | 0.0 |
| Thixcin R | 0.37 | 0.75 | — | — | — |
| Petrolatum | — | — | 4.125 | — | — |
| Palmitic acid | — | — | 0.75 | — | — |
| Superhartolan | — | — | 0.375 | — | — |
| Lather volume by cylinder shake method | Less than 5 cc | Less than 5 cc | Less than 5 cc | Less than 5 cc |  |
| Zein solubility | <0.08 wt. % | <0.08 wt. % | <0.08 wt. % | <0.08 wt. % | 0.05 wt. % |
| Oily/greasy wet-skin feel | None | Medium | Low | None | None |
| Moisturized skin feel 15 to 20 minutes after rinsing and pat dry | Medium | Medium to high | Medium | None | None |

An expert sensory panel under the standard conditions described in the Test Methods section evaluated the sensory properties of the above compositions. Two key sensory properties were assessed: wet-skin feel during rinsing (oily-greasy feel), and skin feel after the skin was dry (moisturized feel). These perceived attributes of the 6 samples by the expert sensory panel are summarized at the bottom of Table 3. The three composition that contain a structured oil phase in the droplet size range disclosed herein are perceived to deliver a medium to high level of moisturization to the skin without excessively oily skin during rinsing (Examples 3A–C). The comparative Examples 3D, and 3E do not provide a perceivable moisturizing effect on dry skin again illustrating that it is the presence of the dispersed structured oil phase of the correct droplet size that is essential to the performance of the composition.

Example 4

Comparison with Commercial Compositions Disclosed in the Art

This example illustrates one advantage of the wet-skin treatment compositions disclosed herein over prior art compositions, namely that they can provide moisturization without an excessively greasy feel during use.

An expert sensory evaluation was carried out comparing the composition of Example 3B (Table 3) with a composition disclosed in the U.S. Pat. No. 5,928,632 that contained mineral oil thickened with a combination of butylene/ethylene/styrene and ethylene/propylene/styrene copolymers. The results are shown in Table 4.

The composition containing polymer-thickened mineral oil, although providing a medium degree of moisturized skin

TABLE 4

|  | Composition of Example 3B | Oil-in-water emulsion according to U.S. Pat. No. 5,928,632[a] |
|---|---|---|
| Ease of Rinsing | Easy to rinse | Very difficult to rinse |
| Oily./Greasy Wet-Skin feel | Medium | Very high |
| Perceived degree of moisturization after drying | Medium to high | Medium |

[a]Oil phase comprised mineral oil and octyl isonanoate and butylene/ethylene/styrene and ethylene/propylene/styrene copolymers.

Example 5

Effect of Oil Composition on Wet-Skin Feel

This example illustrates the use of sensory modifiers to change the perceived wet skin feel of the compositions according to this invention prepared with various skin compatible oils. In these examples, polybutene (Indopol H1500) was used to modify the wet-skin feel of the deposited viscous oils. All the samples were prepared according to the procedures described in Example 1. Polybutene is premixed with the structured oil phase before adding this phase into aqueous phase. The results shown in Table 5 clearly show that the wet-skin feel of provided by the treatment composition can be changed from an oily/greasy feel to non oily/greasy, very draggy rinse feel by replacing 30 wt. % of the total structured oil phase with polybutene. Preferred level and type of polybutene to deliver the most desired wet-skin feel depends on consumer's bathing habit and expectation and can be tailored by one skilled in the art with minimal experimentation.

TABLE 5

|  | Example 5A | Example 5B | Example 5C | Example 5C |
|---|---|---|---|---|
| Carbopol Pemulene TR1 | 0.46 | 0.46 | 0.43 | 0.43 |
| KOH | 0.24 | 0.24 | 0.22 | 0.22 |
| Alkyl polyglucoside Plantarem 2000 | 0.925 | 0.925 | 0.85 | 0.85 |
| Glycerin | 5.55 | 5.55 | 5.2 | 5.2 |
| Perfume | 0.37 | 0.37 | 0.34 | 0.34 |
| Glydant plux | 0.185 | 0.185 | 0.17 | 0.17 |
| DI water | 84.76 | 84.7 | 77.8 | 77.8 |
| Sunflower seed oil | 2.25 | 1.58 | 14.25 | 12.6 |
| Thixcin R | — | — | 0.75 | 0.9 |
| Petrolatum | 4.13 | 2.89 | — | — |
| Palmitic acid | 0.75 | 0.53 | — | — |
| Superhartolan | 0.375 | 0.253 | — | — |
| Indopol H1500 Polybutene | — | 2.25 | — | 4.5 |
| Oily/greasy wet-skin feel | Low | None | Medium | None |
| Draggy wet-skin feel | Low | High | None | High |
| Moisturized skin feel 15 to 20 minutes after pat dry | Medium | Medium to high | Medium to high | Medium |

Example 6

This example illustrates the wide range of structurants that can be employed with various preferred classes of skin compatible oils disclosed herein. Same procedure described in Example 1 was used to prepare all the examples. Phase A, a carbopol-structured aqueous phase, and phase B, thickened-oil premix, were prepared first. Phase B was then injected into phase A using a syringe and passed through screen with 200 micrometer opening twice to make in-shower conditioners containing oil droplets with average particle size larger than 5 micrometers. All the samples are easy to rinse off and provide very good after wash soft smooth moisturizing skin feel.

TABLE 6

| EXAMPLES COMPOSITION | 6A | 6B | 6C | 6D | 6E | 6F | 6G |
|---|---|---|---|---|---|---|---|
| Phase A | | | | | | | |
| Carbopol Pemulen TR1 | 0.35 | 0.35 | 0.35 | 0.35 | 0.35 | 0.35 | 0.35 |
| KOH | 0.189 | 0.189 | 0.189 | 0.189 | 0.189 | 0.189 | 0.189 |
| Cocylamidopropyl betaine | 0.5 | 0.5 | 0.5 | 0.5 | 0.5 | 0.5 | 0.5 |
| Glycerin | 6.0 | 6.0 | 6.0 | 6.0 | 6.0 | 6.0 | 6.0 |
| Perfume | 0.50 | 0.50 | 0.50 | 0.50 | 0.50 | 0.50 | 0.50 |
| Glydant plux | 0.20 | 0.20 | 0.20 | 0.20 | 0.20 | 0.20 | 0.20 |
| DI water | 77.26 | 77.26 | 77.26 | 77.26 | 77.26 | 77.26 | 72.26 |
| Phase B | | | | | | | |
| Sunflower seed oil | 5.25 | 5.25 | — | — | — | 6.0 | 8.0 |
| Isopropylpalmitate | — | — | 6.0 | 10.5 | — | — | — |
| Mineral oil | — | — | — | — | 10.5 | — | — |
| Petrolatum | 9.0 | 9.0 | 9.0 | — | — | 7.5 | 12.0 |
| Paraffin wax (melting point: 53–57° C.) | 0.75 | — | — | — | — | — | — |
| Stearamidopropyl dimethylamine (Lipamine SPA) | — | 0.75 | — | — | — | — | — |
| Bentone Gel MIO V (hydrophobic clay) | — | — | — | 4.5 | 4.5 | — | — |
| Beewax | — | — | — | — | — | 1.5 | — |

Example 7
Wet-Skin Treatment Composition Providing UV Protection

This example illustrates a wet-skin treatment composition according to the principles disclosed herein that provides an additional functional skin care benefits beyond moisturization, namely UV protection. The procedures according to Example 1 was used to prepare Example 7 whose composition is shown in Table 7. Example 7 contains a common organic hydrocarbon UV sunscreen, Parsol MCX that was structured with petrolatum before dispersing it in the aqueous phase. Sun protection factor was determined by a standard in-vivo protocol. The results show that the composition of Example 7 contains 4% Parsol MCX provided a SPF equal to 2.2.

TABLE 7

| FULL CHEMICAL NAME | Example 7 % ACTIVE |
|---|---|
| Polyacrylic acid polymer Carbopol | 0.4 |
| KOH | 0.21 |
| Alkylpolyglycoside | 0.8 |
| Glycerin | 6 |
| Petrolatum | 12 |
| Polybutene | 4 |
| 2 ethylhexyl-p-methoxycinnamate | 4 |
| DMDM HYDANTOIN | 0.2 |
| Perfume | 0.5 |
| Deionized water | 71.9 |
| SPF (sun protection factor) | 2.2 | pH: 6.0–7.0

Example 8
Various Compositions

Additional compositions exemplifying the invention are given in Table 8. All compositions have a droplet size between 20 and 200 microns and the structured oil phase has a viscosity between 200 and 2000 poise at a shear rate of 1 Sec-1.

TABLE 8

| EXAMPLES COMPOSITION | 8A | 8B | 8C | 8D | 8E | 8F | 8G | 8H |
|---|---|---|---|---|---|---|---|---|
| Oil | | | | | | | | |
| Soybean oil | 14.25 | — | — | 10 | — | 2 | — | 3 |
| Mineral oil | — | 4.0 | — | — | — | — | 5 | — |
| Isopropyl palmitate | — | — | 3 | — | — | — | 5 | — |
| Sunflower seed oil | — | — | 7 | — | 9.2 | 10.5 | 2 | — |
| Silicone oil | — | — | 4 | — | — | — | 3 | — |
| Poly alphaolefin oil | — | — | — | 4 | — | — | — | — |
| Structurant | | | | | | | | |
| Hydrophobic Clay | — | — | — | — | — | 4.5 | — | — |
| Thixcin R | 0.75 | — | 0.75 | 1.0 | — | — | — | — |
| Petrolatum | — | 6.0 | — | — | — | — | — | 12 |
| Hydrophobic Silica | — | — | — | — | 0.8 | — | 2.0 | — |
| Dispersion stabilizer | | | | | | | | |
| Pemulen TR1 | — | — | 0.3 | — | — | — | — | 0.5 |
| Xanthan gum | 0.4 | 0.1 | — | — | — | — | 0.2 | — |
| Carbopol ETD2020 | — | — | — | 0.3 | 0.1 | 0.2 | 0.1 | — |
| Laponite XLS | — | — | — | — | 0.4 | — | — | — |
| Cab-O-sil | — | 1.0 | — | — | — | — | — | — |
| Structure Solan | — | — | — | — | — | 0.6 | — | — |
| Emulsifier | | | | | | | | |
| Alkyl polyglycoside | — | 0.5 | 3.0 | — | — | — | 0.3 | — |
| Cocamidopropyl betaine | — | — | — | 0.5 | 0.1 | — | — | — |
| Na cetearyl sulfate | 3.0 | — | — | — | — | — | — | — |
| Cetyl alcohol/Ceteareth-20 | 2.0 | — | — | — | — | 3.5 | 5.0 | — |
| Benefit agent | | | | | | | | |
| Glycerol | 10 | 40 | 3.0 | 5.0 | 5.0 | 5.0 | 5.0 | 5.0 |
| Cholesterol | — | — | 2.0 | 0.1 | — | — | — | — |
| Vitamin A and E | — | — | 0.2 | 0.5 | — | — | — | — |
| Niacinamide | — | — | — | — | 2.0 | — | — | — |
| Triclosan | — | — | — | — | — | 1.0 | — | — |
| Eucalyptus oil | 1.0 | — | — | — | — | — | — | — |
| Menthol | — | — | — | — | — | — | 0.2 | — |
| Parsol MCX | — | — | — | — | — | — | — | 4.0 |
| Parsol 1789 | — | — | — | — | — | — | — | 2.0 |
| Perfume | 0.3 | 1.0 | 0.5 | 0.2 | 0.4 | 0.5 | 0.5 | 0.5 |
| Water | to 100 | to 100 | to 100 | to 100 | to 100 | to 100 | to 100 | to 100 |

*pH was adjusted with KOH solution to 6.0 to 7.0

Example 9
Effect of Wet-Skin Treatment Composition on Visual Dryness

This example demonstrates that the wet-skin treatment compositions deliver a significant enduring reduction in the dryness of skin. Examples 9A–9C whose compositions are shown in Table 9 were prepared according to the procedures of example 1. These compositions were evaluated by in the Controlled Application Leg dryness test described in the methods section. Dryness was evaluated 4 hours after application. The decrease in dryness relative to the initial baseline is shown in the last row of Table 9. Examples 9B, 9C and 9D provide significant reductions in dryness after 4 hours. The magnitude of the decrease in dryness produced by these compositions is twice as large as a control composition (9A) that does not have a structured oil phase.

TABLE 9

| | Example | | | |
|---|---|---|---|---|
| | 9A | 9B | 9C | 9D |
| | 253 | 914 | 438 | 760 |
| FULL CHEMICAL NAME | % | % | % | % |
| Polyacrylic acid polymer | 0.43 | 0.43 | 0.43 | 0.43 |
| Petrolatum | — | — | 12 | 8.25 |
| Superhartolan | — | — | — | 0.75 |

TABLE 9-continued

| | Example | | | |
|---|---|---|---|---|
| | 9A | 9B | 9C | 9D |
| | 253 | 914 | 438 | 760 |
| FULL CHEMICAL NAME | % | % | % | % |
| Prifrac 2960 | — | — | — | 1.5 |
| Thixcin R | — | 0.75 | — | — |
| Sunflower seed oil | 15 | 14.25 | 3 | 4.5 |
| Alkylpolyglycoside | 0.75 | 0.75 | 0.75 | 0.75 |
| Glycerin | 0.52 | 0.52 | 0.52 | 0.52 |
| KOH | 0.24 | 0.24 | 0.24 | 0.24 |
| DMDM HYDANTOIN | 0.2 | 0.20 | 0.20 | — |
| Perfume | 0.5 | 0.5 | 0.5 | 0.5 |
| Deionized water | To 100 | To 100 | To 100 | To 100 |
| Mean Decrease in Dryness relative to baseline 4 hrs after treatment. (average of 3 days) | 0.203 | 0.37 | 0.49 | 0.47 |

Example 10
Effect of Wet-Skin Treatment Composition on Transepidermal Water Loss (TEWL)

This example demonstrates that the wet-skin treatment compositions disclosed herein deliver a significant and enduring reduction in transepidermal water loss (TEWL).

Baseline TEWL were obtained before product application. 20 microliter product was applied to wet test site (4 cm$^2$) for 30 seconds and allow to stay for an additional 30 seconds. The site was then rinsed for 15 seconds using a squeeze bottle and padded dry. The TEWL value was measured again 1 hour after product application. Three subjects were tested and the average results are listed in Table 10.

Examples 10A–10C whose compositions are shown in Table 10 were prepared and evaluated by transepidermal water loss test as described above (see Methods Section for details). Examples 10A and 10B contain preferred compositions of the invention, large droplet oil dispersions of crystal-thickened sunflower seed oil in a carbopol structured aqueous gel. Example 10C is deionized water used as a control. TEWL was evaluated 1 hour after application. Temperature and relative humidity of the room were 21° C. and 23% RH respectively. The decrease in TEWL relative to the initial baseline is shown in the last row of the table. Examples 10A and 10B provide reductions in TEWL after 1 hour and their effects are larger than water (10C).

TABLE 10

| Sample FULL CHEMICAL NAME | 10A % Active | 10B % Active | 10C % Active |
| --- | --- | --- | --- |
| Polyacrylic acid polymer (Carbopol ETD 2020) | 0.3 | 0.3 | — |
| Sunflower seed oil | 5.5 | 9.5 | — |
| Thixcin R | 0.29 | 0.50 | — |
| Alkylpolyglycoside | 0.5 | 0.5 | — |
| Glycerin | 6.0 | 6.0 | — |
| KOH | 0.15 | 0.15 | — |
| Propyl p-hydroxybenzoate | 0.10 | 0.10 | — |
| Methyl p-hydroxybenzoate | 0.15 | 0.15 | — |
| Perfume | 1.0 | 1.0 | — |
| Deionized water | To 100 | To 100 | 100 |
| Mean reduction in TEWL (1 hour after product application) | 1.8 | 2.4 | −1.3 |

PH: 6.0 to 7.0
*here, there is increase in water loss.

Example 11

Effect of Wet-Skin Treatment Composition on Skin Hydration

This example demonstrates that the wet-skin treatment compositions disclosed herein deliver a significant and enduring improvement in skin hydration.

Baseline corneometer readings were obtained on the test site before product application. 20 microliters product was applied to wet test site (4 cm$^2$) for 30 seconds and allow to stay for an additional 30 seconds. The site was then rinsed for 15 seconds using a squeeze bottle and pad dried. One hour after product application, the test sites were wiped to remove surface oil using dry tissue. Corneometer value was then measured. Three subjects were tested and average results were listed in Table 11.

Examples 11A–11C whose compositions are shown in Table 11 were prepared and evaluated by Corneometer test described in the Methods Section. Examples 11A and 11B are the preferred in shower skin conditioner of the invention. Again, 11C is deionized water used as control. Corneometer value was evaluated 1 hour after application. Temperature and relative humidity of the room were 21° C. and 23% RH respectively. The increase in corneometer reading relative to the initial baseline is shown in the last row of Table 11. Examples 11A and 11B provide increase in Corneometer reading after 1 hour and their effects are larger than water (11C).

TABLE 11

| Sample FULL CHEMICAL NAME | 11A % Active | 11B % Active | 11C % Active |
| --- | --- | --- | --- |
| Polyacrylic acid polymer (Carbopol ETD 2020) | 0.3 | 0.3 | — |
| Sunflower seed oil | 5.5 | 9.5 | — |
| Thixcin R | 0.29 | 0.50 | — |
| Alkylpolyglycoside | 0.5 | 0.5 | — |
| Glycerin | 6.0 | 6.0 | — |
| KOH | 0.15 | 0.15 | — |
| Propyl p-hydroxybenzoate | 0.10 | 0.10 | — |
| Metyl p-hydroxybenzoate | 0.15 | 0.15 | — |
| Perfume | 1.0 | 1.0 | — |
| Deionized water | To 100 | To 100 | 100 |
| Mean increase in Corneometer Reading (1 hour after product application) | 10.2 | 11.0 | 4.0 |

Examples 12A–12E
In Shower Conditioner Containing Structured Oil with Dispersed Phase In order to demonstrate compositions with structured oil comprising a dispersed phase, applicants prepared example comprising 12A–12E as noted in Table below.

| | 12A | 12B | 12C | 12D | 12E |
| --- | --- | --- | --- | --- | --- |
| Carbopol-Structured Aqueous Gel | | | | | |
| Pemulen TR1 (Polyacrylate structurant) | 0.35 | 0.35 | 0.35 | 0.35 | 0.35 |
| Glycerin | 6.0 | 6.0 | 6.0 | 6.0 | 6.0 |
| Glydant plus | 0.2 | 0.2 | 0.2 | 0.2 | 0.2 |
| Alkyl polyglucoside | 0.5 | 0.5 | 0.5 | 0.5 | 0.5 |
| Perfume | 1.0 | 1.0 | 1.0 | 1.0 | 1.0 |
| Lytron 680 (Polystyrene opacifier) | 0.5 | 0.5 | 0.5 | 0.5 | 0.5 |
| KOH (40% solution) | 0.45 | 0.45 | 0.45 | 0.45 | 0.45 |
| Deionized water | 81.0 | 81.0 | 81.0 | 81.0 | 81.0 |
| Crystal-Structured Viscous Oil Containing Water Dispersible Solid Particle | | | | | |
| Petrolatum | 7.6 | 7.6 | 7.6 | 6.4 | 6.4 |
| Sunflower seed oil | 1.9 | 1.9 | 1.9 | 1.6 | 1.6 |
| Spectratek 100 × 100 microns Geometric silver glitter | 0.5* | — | — | — | — |
| Timiron MP 1005 (15 microns) from Rona | — | 0.5 | — | — | — |
| Timiron MP-1001 Supersheen cosmetic pigment, 5 to 25 microns from Rona | — | — | 0.5 | — | — |
| Talc, Cimpact 710. 1 to 3 microns from Luzenac America | — | — | — | 2.0 | — |
| Titan M212, submicron water-dispersible TiO2 from Preserpse | | | | | 2.0 |

*For purposes of invention, dispersed inside structured oil; for purposes of comparative, delivered in aqueous phase.

All the samples were prepared using the method similar to the one described in Example 1. An oil premix containing crystal-structured viscous oil and cosmetic grade particles was prepared by mixing petrolatum and sunflower seed oil to form a uniform clear mixture at 70° to 80° C. (structured oil). The cosmetic grade solid particles were then added into the petrolatum/sunflower seed oil mixture and mixed while cooling. The mixture was cooled below 40° C. to form a viscous, stable particle-in-oil dispersion, and was injected into and mixed with the carbopol-structured aqueous gel to form large lumps of particle-in-oil dispersion with size larger than 1000 microns. The mixture was then passed through screens of 500 microns opening twice to make conditioners containing droplets larger than 100 microns with solid particles stably dispersed inside the large oil droplets.

A comparative example with composition same as Example 12A was prepared to show the enhanced deposition of solid particles from a rinse off product using particle-in-oil dispersion as described in the invention. In this example, instead of dispersing the Spectratek glitter inside the structured oil, the 100×100 microns glitters were added and dispersed directly into the Carbopol structured aqueous gel. After dispersing the Spectratek glitters in the Carbopol gel, petrolatum/sunflower seed oil mixture was added and mixed with the Carbopol gel. The mixture was then passed through screen of 500-micron opening twice to make the comparative example in which the glitter and the viscous oil were dispersed in the Carbopol gel as separate particles.

Deposition of Spectratek glitter on the skin from Example 12A was compared to the comparative example on the volar part of forearm. The forearm was cleaned with about 0.5 grams of surfactant solution containing 12 wt. % NaLES and 3 wt. % Na cocamidopropyl betaine. Right after rinsing off the surfactant solution, 0.5 grams of the sample was applied and rubbed on the volar part of the forearm for 20 seconds followed by 30-second rinsing with tap water. The skin was then slightly patted dry with a paper towel. Arm treated with Example 12A had much higher amount of visible shiny particles left on the skin than the arm treated with the comparative example. This has clearly showed that retention of solid particles from a shower conditioner can be enhanced using stable particle-in-oil dispersion as claimed in the invention.

We claim:

1. A process for moisturizing and protecting skin comprising the steps of:
   (A) washing and/or rinsing the skin to wet and remove dirt and debris;
   (B) thereafter applying to wet skin an effective amount of a water-activated wet skin treatment composition comprising:
      (i) an aqueous phase comprising water and a dispersion stabilizer, wherein said dispersion stabilizer is selected from the group consisting of inorganic dispersion stabilizers, polymeric dispersion stabilizers, organic dispersion stabilizers having a molecular weight lower than about 1000 Daltons and capable of forming a network in the aqueous phase that immobilizes a dispersed structured oil phase, and mixtures thereof; and;
      (ii) a structured oil phase comprising:
         (a) a skin compatible oil,
         (b) a structurant that forms a stable network comprising particles having an average size below about 25 microns which particles are present in said liquid skin compatible oil at a temperature below 35° C. in an amount sufficient to have a viscosity of 100 to 500 poise measured at 1 sec$^{-1}$ at 25° C. and wherein said structurant is selected from the group consisting of organic structurants having MW less than 5000 Daltons, inorganic structurants or mixture of said organic and inorganic structurants that is capable of forming a 3-dimensional network to build up the viscosity of said skin compatible oil;
         (c) 0.01 to 45% of dispersed phase based on total structured oil phase;
      wherein said oil phase is dispersed in said aqueous phase to form an oil-in-water emulsion having a weight average oil droplet size of 5 to 1000 microns;
      wherein said structured oil phase is retained on the skin as measured by a skin retention efficiency index of at least 0.15 as determined in the in-vitro skin retention test;
      wherein said oil-in-water emulsion has an irritation potential measured below 0.3 on the zein solubility scale using a zein solubility test; and
      wherein said emulsion has a foam volume below 5 cc measured using a solution shake test;
   C) optionally removing excess water-activated treatment composition by further rinsing the skin; and
   D) drying the skin.

2. A process according to claim 1, wherein the compatible oil is a hydrocarbon oil, an ester oil, or a silicone oil.

3. A process according to claim 1, wherein the organic structurant forms a solution in said skin compatible oil at a temperature greater than 40°C.

4. A process according to claim 1, wherein the structured oil phase in the oil-in-water emulsion has a weight average oil droplet size in the range of 20 to about 500 microns.

5. A process according to claim 1, wherein the structured oil phase has a viscosity in the range of 200 to 2000 poise at a shear rate of 1 sec-1 and a temperature of 25° C.

* * * * *